United States Patent
Yokoyama et al.

(10) Patent No.: US 6,995,249 B1
(45) Date of Patent: Feb. 7, 2006

(54) NUCLEIC ACID CAPABLE OF BINDING SPECIFICALLY TO RAS TARGET PROTEIN

(75) Inventors: Shigeyuki Yokoyama, Tokyo (JP); Ichiro Hirao, Asaka (JP); Kensaku Sakamoto, Tokyo (JP)

(73) Assignee: Japan Science and Technology Corporation, Kawaguchi (JP)

( * ) Notice: Subject to any disclaimer, the term of this patent is extended or adjusted under 35 U.S.C. 154(b) by 0 days.

(21) Appl. No.: 09/529,397

(22) PCT Filed: Aug. 13, 1999

(86) PCT No.: PCT/JP99/04399

§ 371 (c)(1),
(2), (4) Date: Sep. 26, 2000

(87) PCT Pub. No.: WO00/09684

PCT Pub. Date: Feb. 24, 2000

(30) Foreign Application Priority Data

Aug. 24, 1998 (JP) ............... 10-242596
Nov. 24, 1998 (JP) ............... 10-333284

(51) Int. Cl.
C07H 21/02 (2006.01)
C07H 21/04 (2006.01)

(52) U.S. Cl. .......... 536/23.1; 536/24.1; 536/24.3; 536/24.32

(58) Field of Classification Search ......... 536/23.1, 536/24.3, 24.32, 24.33; 435/6
See application file for complete search history.

(56) References Cited

U.S. PATENT DOCUMENTS

| 5,582,995 | A | * | 12/1996 | Avruch et al. ............... 435/7.1 |
| 5,597,719 | A | * | 1/1997 | Freed et al. ................. 435/194 |
| 6,521,407 | B1 | * | 2/2003 | Warenius et al. ............. 435/6 |
| 2003/0170751 | A1 | * | 9/2003 | Sherman et al. .......... 435/7.23 |

FOREIGN PATENT DOCUMENTS

| WO | WO 92/14843 | 9/1992 |
| WO | WO 94/29727 | 12/1994 |
| WO | WO 97/34146 | 9/1997 |

OTHER PUBLICATIONS

Hudson et al., "Screening for inhibitors or ras-protein partner interactions- using a ras-binding domain coated on scintillation plates and tritium-labelled GTP," *Zeneca Pharm. Cancer Res. Dept.* (1995) Abstract XP-002246369.

Michiko Kimoto et al., "RNA aptamers that specifically bind to the Ras-binding domain of Raf-1", FEBS Letters, 441(2): 322-326 (1998).

Walter Kolch et al., "Inhabition of Raf-1 signaling by a monoclonal antibody, which interferes with Raf-1 activation and with Mek substrate binding", Oncogene, 13(6):1305-1314 (1996).

Andrew D. Ellington et al., "In vitro selection of RNA molecules that bind specific ligands", Nature, 346(6287): 818-822 (1990).

Craig Tuerk et al., "Systematic evolution of ligands by exponential enrichment: RNA ligands to bacteriophage T4 DNA polymerase", Science, 249(4968):505-510 (1990).

* cited by examiner

Primary Examiner—Kenneth R. Horlick
Assistant Examiner—Cynthia Wilder
(74) Attorney, Agent, or Firm—Edwards & Angell LLP; Peter F. Corless

(57) ABSTRACT

A novel nucleic acid (aptamer) which binds specifically to the target protein of Ras, more particularly, a novel RNA aptamer which binds specifically to Raf-1; a method for screening an RNA capable of binding specifically to the target protein of Ras which comprises selecting an RNA capable of binding to the target protein of Ras from a pool of RNAs having various base sequences; a method for regulating the signal transduction causing the proliferation or differentiation of cells by using the above-described nucleic acid; and medicinal compositions with the use of the same.

5 Claims, 4 Drawing Sheets

Starting RNA:
5'-GGGAGAUCAGAAUAAACGCUCAA[-60N-]UUCGACAUGAGGCCCCUGCAGGGCG-3'

PCR primer 1:
5'-GCCGGAATTCTAATACGACTCACTATAGGGAGATCAGAATAAACGCTCAA-3'
        EcoRI    T7 promoter PCR primer 2:
5'-CGCCCTGCAGGGGCCTCATGTCGAA-3'
        PstI

Figure 1

| RNA clone[a] | Sequence[b] | RNA Bound(%)[c] |
|---|---|---|
| Group 1 | | |
| 21.01 (6) | CUGAUCAAUGGCGUACAAUGGAUUCGUUCUCAUAACCAAAACCCUACCCCUUGACUGA | 42 |
| 21.02 | CUGAUCAAUGGCGUACAAUGGAUUCGUUCUCAUAACCAAAACCCUACCCCUUGACUGA | |
| 21.03 (4) | CUGAUCAAUGGCGUACAAUGGAUUCGUUCUCAUAACCAAAACCCUACCC-UGGACUGA | |
| 21.04 | CUGAUCAAUGGCGUACAAUGGAUUCGCUCUCAUAACCAAAACCCUACCCCUUGACUGC | |
| 21.05 | CUGAUCAAUGGCGUACAAUGGAUUCGUUCUCAUAACCAAAACCCUACCCCUUGACUGC | |
| 21.06 | CUGAUCAAUGGCGUACAAUGGAUUCGUUCUCAUAACCAAAACCCUACCUCUUGGACUGC | 46 |
| 21.07 | UUGACUCAAUGGCGUACAAUGGAUUCGUUCUCAUAACCAAAACCCUACCCCUUGACUGU | 46 |
| 21.08 | UUGAAGAUCAAUGGCAAUGGAUUCG--AUCAUAACCCGAAGUUUUAAACACUCUUACCUGUA | 12 |
| Group 2 | | |
| 21.09 | UCGAGUCCACGAACAUUACAUAUUGAACACUCAGCACCGAACAUGCUUAGUACUAUCC | 3 |
| 21.10 | UAUUACCAUAGCCUUGAGGUUAAACAAUUAGCACCUGAAAUACACGAAUACACUCA | 0.2 |
| 21.11 (2) | CUUGAGCCAAUUAAAAGAUUUACAACAAGAACAUGAACGUGACAGCGAUAAUAACGA | |
| 21.12 | GCGACAAGCAGCAGAAUAAAGUUGAGCGCAACGCCUACAGAACCAAAUUAACAUGUAUG | |
| 21.13 | UCGAAAGUAAGUCCGAUACUAUUAUUUAGCAGGAGUAAUAGUAAUCAAAUAAG | |
| 21.14 | GCAGUAAUCCACUUGUAAUUGAAUGAUGCCAUAUUGAAUCUUCGCAAUGUACCUAACACUAAUCAG | |
| 21.15 | CGUAGUAGCACACCAUGAUAAAUUACAACAGAUAACCUAUACUCUCUUGAACUAACACAUAAUCAG | |
| 21.16 | GAAUGACUAAAUAAUUACAACAGAUAACCUAGAAAUGCUUUGCUUUUGGUUAA | 1 |
| 21.17 | UCUUCGAAGUCCAUGACUGCAAAACCAGAUAGUCCUAAUCCAAUAUCAGUCCCAAGUA | |
| 21.18 | ACACUCUAAAUUGUGUACUUAGGGAGUAACGCAACGAAGACGUGACAAGGAUAAAG | 0.5 |
| 21.19 | UUUGCCCUCGACGGUCUGCGAAAUAGAACGCAAAUUCAAUGCAUCUCAUUAGUACACUUAUCAGGUU | |
| 21.20 | GUCGCAGCAGAAAUAUCGAGUAAUCAUCGAAUCAAACCUCAUAUAACCUUAUACACUUUCUAAACUA | 0.7 |
| 21.21 | CGAACAUCUGGAGUAGAGCAGUUCAAGAUGGCAUUCAUUUGAAAGAAAGGUUGGUGAC | |
| 21.22 | GGGUAAGGGUGAGCAGUUCAAGAUCAAGAUGGUAACCGGCAUUCAUUGAGAAAGGUUGGUAGC | 1.3 |
| 21.23 | GGGUAAGGGUGAGCAGUUCAAGUGAGAGAUAUAAGGUUAUGUUAUGUGCGAACGG | |
| 21.24 | CUUGGUAGUAGUCAAGUGAGAGAUAUAAGGUUAUGUUAUGUGCGAACGG | |

Figure 2

NUCLEIC ACID CAPABLE OF BINDING SPECIFICALLY TO RAS TARGET PROTEIN

TECHNICAL FIELD

The present invention relates to novel nucleic acids (aptamer) which are specifically bound to target proteins of Ras. More particularly, the present invention relates to novel RNA aptamers which are specifically bound to Raf-1. Further, the present invention relates to control of signal transduction that induces proliferation or differentiation of cells using the nucleic acids of the present invention, and to a pharmaceutical composition using the same.

BACKGROUND OF THE INVENTION

Ras is a guanine nucleotide binding protein, and participates in signal transduction of cells. When a receptor of cells is activated, "GDP binding Ras" in cells becomes "GTP binding Ras".

This "GTP binding Ras" is bound to "target proteins of Ras" such as Raf-1, B-Raf, RGL, Ral GDS, MEKK, P13KK and the like. These "target proteins of Ras" have a Ras binding domain (RBD) to which the GTP binding Ras can be bound, and the GTP binding Ras is bound to this domain of these "target proteins of Ras" to transmit necessary signals into cells.

Ras is a key protein of intracellular signal transduction, and the "target proteins of Ras", such as Raf-1, are a center of the intracellular signal transduction system in which signals from Ras are transmitted according to the types.

Accordingly, a substance capable of specifically blocking the binding domain with the GTP binding Ras in the "target proteins of Ras", if any, can specifically inhibit an intracellular signal transduction system by Ras, and it is useful to treat or prevent various diseases triggered by the signal transduction. For example, with respect to tumor cells, proliferation or differentiation of tumor cells can be inhibited by specifically controlling the signal transduction that induces proliferation or differentiation with the "target cells of Ras" to treat cancers or inhibit metastasis.

By the way, Ras-1, one of the "target cells of Ras" is a serine/threonine protein kinase present in a cytoplasm, and the activity is induced by interaction with the GTP binding Ras. The activated Raf-1 phosphorylates MEK (MAPK/ERK kinase), and then MEK phosphorylates ERK to transmit signals into a nucleus (Daum, G., et al., (1994) Trends Biochem. Sci. 19, 474–480; Avruch, J., et al., (1994) Trends Biochem. Sci. 19, 279–283).

In order to elucidate such an intracellular signal transduction system of Raf-1, a method of selectively inhibiting the function of Ras or Raf-1 has been utilized (deVries-Smits, A. M., et al., (1992) Nature 357, 602–604). These studies include inhibition of the Ras function with a Raf-1 mutant free from a kinase activity (Kolch, W., et al., (1991) Nature 349, 426–428), inhibition of a Raf-1 kinase with an antibody bound to a kinase domain of Raf-1 (Kolch, W., et al., (1996) Oncogene 13, 1305–1314) and the like.

However, these inhibitors do not specifically inhibit a specific part of a signal transduction system with Ras or Raf-1, but inhibit many functions such as a function of binding to Ras, a kinase function and the like simultaneously and diversely. Accordingly, a signal transduction system to be inhibited cannot be specified. Thus, individual specific mechanisms of a signal transduction system could not be clarified satisfactorily.

Consequently, the development of a molecular seed capable of specifically inhibiting the binding of Ras to Raf-1 has become important for clarifying the role of the signal transduction system.

At present, a downstream signaling pathway of Ras has not been completely clarified. When such a molecular seed is developed, it is possible to elucidate the signaling pathway in which Ras participates using a molecular seed capable of specifically inhibiting some specific routes and clarify the signaling pathway with target proteins of Ras in detail. In addition, it is possible to control the intracellular signal transduction. Consequently, various diseases in which the intracellular signal transduction participates, such as tumors and the like, can be treated and prevented.

Meanwhile, the structural analysis of the "target proteins of Ras" in the intracellular signaling pathway in which Ras participates has been conducted. It has been known that the Ras binding domain (RBD) of Raf-1 is located from 51 to 131 residues in the N-terminus of Raf-1 (Vojtek, A. B., et al., (1993) Cell 74, 205–214; Chuang, E., et al., (1994) Mol. Cell. Biol. 14, 5318–5325).

Further, nucleic acid molecular seeds (aptamers), such as an RNA, a DNA and the like, having a high affinity for a certain target, such as proteins, have been isolated by "in vitro selection" methods (Ellington, A. D., et al., (1990) Nature 346, 818–822; Tuerk, C., et al., (1990) Science 249, 505 . 510) (Bock, L. C., et al., (1992) Nature 355, 564–566; Qiu Qiu, Y. L., et al., (1994) Nucleic Acids Res. 22, 5229–5234; Gal. S. W., et al., (1998) Eur. J. Biochem. 252, 553–562; Bell, S. D., et al., (1998) J. Biol. Chem. 273, 14309–14314). Therefore, there is a possibility that an RNA specifically bound to Raf-1 is obtained by applying this method to Raf-1, while the interaction with an RNA is unknown.

DISCLOSURE OF THE INVENTION

The present invention is to provide nucleic acid molecular seeds which can specifically inhibit the binding to "GTP binding Ras" by being specifically bound to a Ras binding domain (RBD) of target proteins of Ras such as Raf-1, B-Raf, RGL, Ral GDS, MEKK, P13K and the like.

In order to clarify the signaling pathway in which the target proteins of Ras participate and the physiological activity provided by the inhibition of the signal transduction, the development of substances which specifically inhibit the binding to Ras having an important role in cells in particular along with Raf-1 by being specifically bound to the target proteins of Ras, in more detail, Raf-1 and which have a strong activity have been in demand. The present inventors have found that a nucleic acid molecular seed specifically bound to the Ras binding domain of the target "target proteins of Ras" can be obtained using the in vitro selection method. For example, it has been possible to obtain a novel RNA aptamer targeting the Ras binding domain (RBD) of Raf-1, one of the "target proteins of Ras" by this method and to determine the RNA sequence thereof. This RNA aptamer can specifically inhibit the binding between Ras and Raf-1.

Accordingly, the present invention is to provide novel nucleic acid molecular seeds bound to a "target protein of Ras", especially, its Ras binding domain (RBD), an agent for controlling a signal transduction system using the nucleic acid molecular seeds, a method of controlling the same, and a pharmaceutical composition containing the same.

More specifically, the present invention is to provide RNA aptamers that bound to a "target protein of Ras", especially its RBD, an agent for controlling a signal transduction system using this RNA aptamer, a method of controlling the same, and a pharmaceutical composition containing the same.

BRIEF DESCRIPTION OF THE DRAWINGS

FIG. 1 shows a sequence of an initial RNA pool in the in vitro selection of the present invention (SEQ ID NO:61) and sequences of PCR primers 1 and 2 (SEQ ID NOs:57 and 58, respectively).

FIG. 2 shows 24 sequences of RNAs obtained from the RNA pool in the 21$^{st}$ round. In the drawing, a random sequence moiety of approximately 60 bases is shown. The overall sequence include the sequences of the 5'- and 3'-termini defined in FIG. 1. Sequences which are the same as that of clone 1 are termed "group 1" (SEQ ID NOs:29–36). The other sequences are termed "group 2" (SEQ ID NOs:37–52). Incidentally, in note (a), the number of clones of ligands isolated respectively is shown in parentheses. In note (b), clone 21.08 (SEQ ID NO:36) indicates that each sequence defined has two mutations. In note (c), percentage of the binding of the RNA ligand to GST-RBD is based on a value measured by the nitrocellulose filter binding assay. Clone 21.01: SEQ ID NO:29. Clone 21.02: SEQ ID NO:30. Clone 21.03: SEQ ID NO:31. Clone 21.04: SEQ ID NO:32. Clone 21.05: SEQ ID NO:33. Clone 21.06: SEQ ID NO:34. Clone 21.07: SEQ ID NO:35. Clone 21.08: SEQ ID NO:36. Clone 21.09: SEQ ID NO:37. Clone 21.10: SEQ ID NO:38. Clone 21.11: SEQ ID NO:39. Clone 21.12: SEQ ID NO:40. Clone 21.13: SEQ ID NO:41. Clone 21.14: SEQ ID NO:42. Clone 21.15: SEQ ID NO:43. Clone 21.16: SEQ ID NO:44. Clone 21.17: SEQ ID NO:45. Clone 21.18: SEQ ID NO:46. Clone 21.19: SEQ ID NO:47. Clone 21.20: SEQ ID NO:48. Clone 21.12: SEQ ID NO:49. Clone 21.22: SEQ ID NO:50. Clone 21.23: SEQ ID NO:51. Clone 21.24: SEQ ID NO:52.

In FIG. 3, a closed circle indicates the use of an RNA of SEQ ID NO:1, a closed square the use of an RNA of SEQ ID NO:7, and a closed triangle the use of an RNA of SEQ ID NO:11.

BEST MODE FOR CARRYING OUT THE INVENTION

Figure 3:
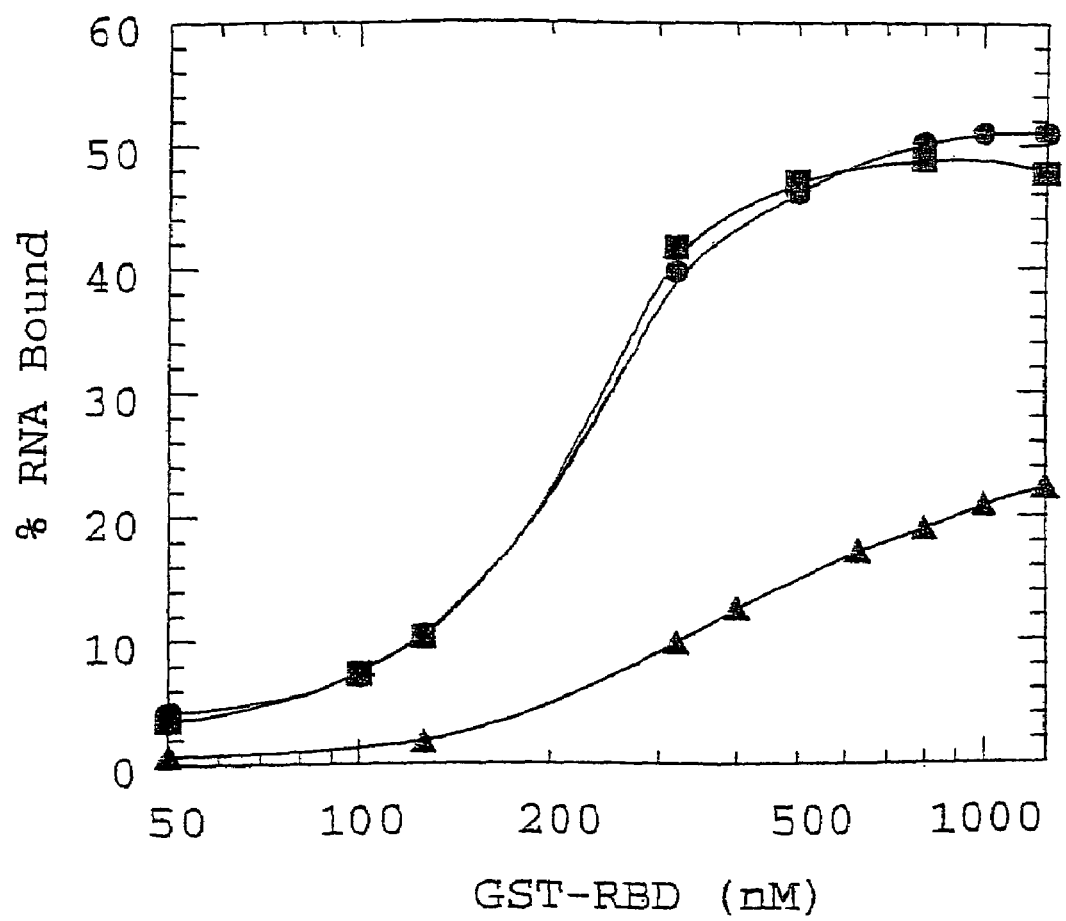
FIG. 3 shows the binding of the RNA ligand to the GST-RBD protein. Percentage of the binding of the RNA ligand to GST-RBD is based on a value measured by the nitrocellulose filter binding assay.

The "target proteins of Ras" of the present invention refers to Ras proteins which participate in the cell signal transduction, preferably a group of proteins forming an intracellular signal transduction system by interacting with GTP binding Ras proteins. Examples of the "target proteins of Ras" of the present invention include Raf-1, B-Raf, RGL, Ral GDS, MEKK, P13K and the like. However, this invention is not limited within the target. The "target proteins of Ras" of the present invention are preferably Raf-1 and the like.

The present invention has clarified that nucleic acid molecular seeds capable of being specifically bound to the foregoing "target proteins of Ras" exist. Accordingly, the nucleic acid specifically bound to the "target proteins of Ras" in the present invention may be an RNA or a DNA. The RNA or the DNA is not particularly limited so long as it is specifically bound to the "target proteins of Ras". Further, the nucleic acid of the present invention may be specifically bound to only one "target protein of Ras" or to two or more "target proteins of Ras".

The size of bases of the nucleic acid molecular seed of the present invention is not particularly limited so long as it is sufficient to allow the specific binding to the "target proteins of Ras". It is between 20 and 300 bases, preferably between 20 and 150 bases, more preferably between 30 and 150 bases, further preferably between 50 and 150 bases. In case the binding specificity is stressed, the longer size is preferable. However, in view of the ease of the procurement in the synthesis method or the like, the shorter size is preferable.

As the nucleic acid molecular seed of the present invention, an RNA containing any one of base sequences, SEQ ID NOs:1–28, preferably SEQ ID NO:1–8 or SEQ ID NOs:25–28 of the Sequence Listing is mentioned.

The RNAs of the present invention shown in the sequence listing have an ability of binding to the "target proteins of Ras". More specifically, the RNAs are characterized in that they are specifically bound to the Ras binding domain (RBD) of Raf-1, and the nucleic acid molecular seed of the present invention is not limited to the base sequence shown in the foregoing SEQ ID NOs:1–28. A seed having a base sequence in which at least one base of SEQ ID NOs:1–28 of the Sequence Listing is deleted and substituted with another base and/or another base is added is also available so long as it has an ability of binding to the "target proteins of Ras".

The nucleic acid molecular seed of the present invention can be one containing these base sequences in the whole or a part of the molecule. For example, a base sequence or another molecular seed may further be added to the nucleic acid molecular seed having the base sequences shown in sequence Nos. 1 to 28 of Sequence Listing unless the ability of binding to the "target proteins of Ras" is inhibited.

These RNAs of the present invention can also be reversely transcribed, as required, into DNAs having complementary base sequences to the RNAs. Accordingly, the present invention relates to nucleic acid molecular seeds such as RNAs, DNAs and the like, containing any one of base sequences of SEQ ID NO:1–28 of the Sequence Listing or a base sequence in which at least one base thereof is deleted and substituted with another base and/or at least one base is added.

The "aptamer" in the present invention refers to a nucleic acid molecular seed capable of being bound to a specific domain of a protein, and the nucleic acid may be an RNA or a DNA. An aptamer made of an RNA is called an "RNA aptamer". Accordingly, in the present invention, the nucleic acid molecular seed in the present invention is also termed an "aptamer". When the nucleic acid is an RNA, it is called an "RNA aptamer".

Incidentally, RNAs comprising approximately 60 bases shown in SEQ ID NOs:29–52 of the Sequence Listing indicate base sequences comprising approximately 60 bases in a central portion of RNAs shown in SEQ ID NOs:1–24. Further, RNAs comprising approximately 45 bases shown in SEQ ID NOs:53 and 54 of the Sequence Listing indicate base sequences comprising approximately 45 bases in a central portion of RNAs shown in SEQ ID NOs:25–28.

Moreover, SEQ ID NOs:55–60 of the Sequence Listing show base sequences of primers used in specific examples of the present invention.

The nucleic acid (aptamer) of the present invention can be produced by various methods. When the base sequence of the aptamer is known, it can be synthesized.

When the base sequence of the aptamer of the present invention is unknown, the aptamer can be produced through selection by the known "in vitro selection" method (Ellington, A. D. et al., (1990) Nature 346, 818–822; Tuerk, C. et al., (1990) Science 249, 505–510). The "in vitro selection" method in the present invention is described.

First, RNAs containing a random base sequence of 20 to 300 bases, preferably 30 to 100 bases, more preferably 30 to 70 bases are produced. These RNAs are produced by transcription from synthetic DNAs containing a random sequence.

A base sequence which is to be a primer in the PCR method is added to the 5'-terminus and the 3'-terminus of the DNAs. In this case, the primer is not particularly limited. A primer having a sequence of cleavage with a restriction endonuclease so as to be able to cleave this primer portion later is preferable. A size of the primer portion is not particularly limited. It is approximately between 20 and 50 bases, preferably between 20 and 30 bases. Further, the primer at the 5'-terminus may be designed such that a promoter sequence of a T7 RNA polymerase is added thereto to enable the transcription reaction from DNA to RNA.

In this manner, the RNA group (RNA pool) having the base sequences as the primer at both termini and the random base sequence in the center is produced by transcription of the DNA.

Subsequently, the RNA in this RNA pool and the "target protein of Ras", for example, Raf-1 or a peptide comprising its binding domain are contacted to separate the RNA bound to the "target protein of Ras". The selected RNA is converted to a cDNA through reverse transcription, and it is simplified by PCR using the primers. The DNA amplified is transcribed into an RNA, and this is returned to the RNA pool.

One cycle, termed a "round", comprises binding with the "target protein" of Ras in the RNA pool, the separation of the bound RNA, reverse transcription, amplification by PCR and transcription of the DNA. That is, one round means that the foregoing round is conducted once.

When the foregoing round using the RNA pool is conducted, the amount of the RNA bound to the "target protein of Ras" in the RNA pool is increased, and further the amount of the RNA having the specific binding base sequence is increased, so that the RNA to be specifically bound can be selected by repeating the round.

Such a round is conducted 5 to 50 times, preferably 5 to 30 times.

The RNA sequences selected by the "in vitro selection" method as described above are determined by a usual method, and this RNA can also be converted to a cDNA through reverse transcription by a usual method. Further, the primer regions can be cleaved as required. In this manner, the aptamers of the present invention can be obtained.

The "in vitro selection" method of the present invention is described in more detail by using Raf-1 as the "target protein of Ras".

The present inventors have prepared a pool of RNAs having a random sequence of approximately 60 bases to select RNAs bound to the Ras binding domain (RBD) of Raf-1. And, the base sequences shown in FIG. 1 were bound to the 3'-terminus and the 5'-terminus of these RNAs. It was presumed that approximately $8 \times 10^{13}$ sequences of RNAs are present in this RNA pool.

Before conducting the selection of the aptamer, the effect of the salt concentration relative to the binding between the RNA pool and Raf-1-RBD was examined. At a low salt concentration, the RNA was non-specifically bound to Raf-1-RBD. However, it was found that the non-specific binding is suppressed by increasing the salt concentration (up to approximately 150 mM). Thus, the present inventors used a phosphate buffer (hereinafter referred to as a "binding buffer") containing 137 mM sodium chloride as a buffer for the selection.

The selection from the 1st to 13th rounds was conducted by the binding between a fusion protein of glutathione S-transferase (GST) and a peptide (RBD) of 51 to 131 of Raf-1 (hereinafter referred to as "GST-RBD") and RNAs using a glutathione-Sepharose 4B matrix. In the 13th round, the binding ability (binding ratio) to the RNA pool was slightly changed from 0.16% at the initial stage of 0.36%.

Successively, the selection using a nitrocellulose filter instead of the matrix was conducted eight times (8 rounds). In the 21st round, the binding ability to the RNA pool was 22%, and the Kd value of the pool relative to the protein GST-RBD was 290 nM.

The sequences of 33 clones were determined from the RNA pool which finished the 21st round. Consequently, 24 different sequences were obtained. The sequences of the portions comprising approximately 60 bases in the 24 sequences of clones are shown in FIG. 2. They were roughly divided into two types, one having a high homology among the sequences (this group is called "group 1") and the other among which no homology, was observed (these are referred to as "group 2").

The sequences of the total sizes (approximately 100 bases) of the 8 types of RNAs (21.01 to 21.08 in FIG. 2) in group 1 are shown in SEQ ID NOs:1–8.

The interaction between the 10 RNAs among them and GST-RBD was examined by a binding assay using a nitrocellulose filter. The results are shown in the right column of FIG. 2 in terms of RNA binding (%). As a result, the RNAs in group 1 showed the satisfactory binding to GST-RBD, whereas the RNAs in group 2 did not show the satisfactory binding. The Kd values of the RNAs shown in SEQ ID NO:1 (21.01 in FIG. 2) and SEQ ID NO:7 (21.07 in FIG. 2) were both 300 nM. Meanwhile, that of the RNA in SEQ ID NO:11 (21.11 in FIG. 2) was a micromol order (refer to FIG. 3). FIG. 3 shows percentages of binding to GST-RBD when using RNAs having SEQ ID NO:1 (closed circle), SEQ ID NO:7 (closed square) and SEQ ID NO:11 (closed triangle) at various concentrations (nM).

Further, the RNA ligands were not bound to GST itself. This indicates that these RNA is bound to the RBD moiety of GST-RBD rather than to the GST moiety.

Figure 4:
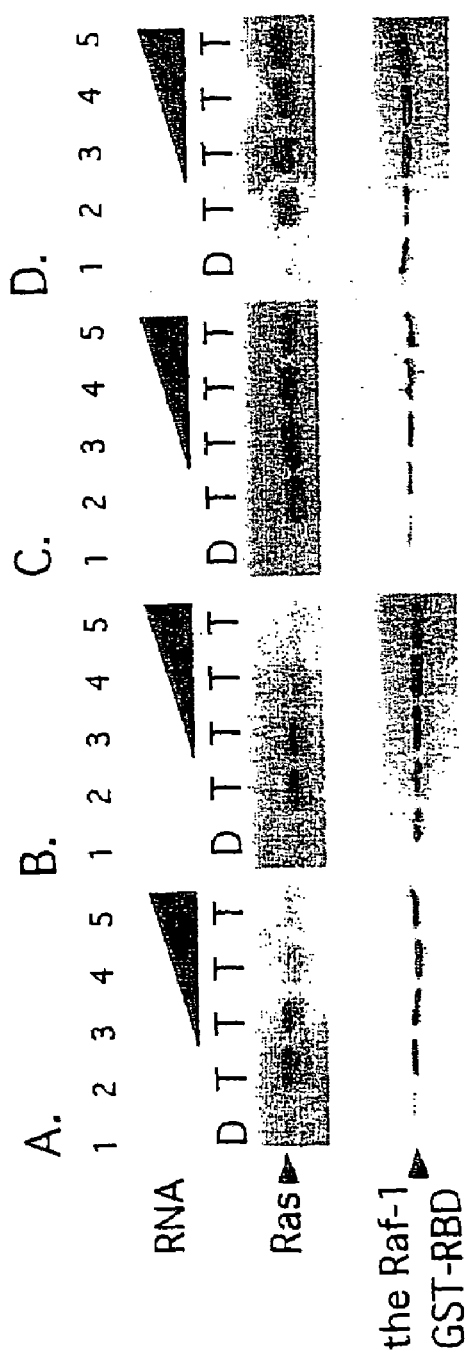
FIG. 4 is a photo that replaces a drawing, showing inhibition of interaction between Ras and GST-RBD by the RNA aptamers. An amount of the Ras protein bound to GST-RBD as measured by immunoblotting with anti-Ras antibody RAS004 is shown on an upper column. An total amount of GST-RBD measured by staining with Coomassie Blue is shown on a lower column. GDP binding (D) or GTPγS binding (T) Ras (2 pmols) and GST-RBD (25 pmols) were incubated in the presence of an RNA in various amounts. A used 21.01 ligand in FIG. 2, B 21.07 ligand in FIG. 2, C 21.11 ligand in FIG. 2, and D 21.12 ligand in FIG. 2.

It was then examined whether the RNA aptamers in group 1 inhibit the interaction between Ras and RBD (refer to FIG. 4). The RNAs having SEQ ID NO:1 (A in FIG. 4), SEQ ID NO:7 (B in FIG. 4), SEQ ID NO:11 (C in FIG. 4) and SEQ ID NO:12 (D in FIG. 4) (corresponding to 21.01, 21.07, 21.11 and 21.12 in FIG. 2, respectively) were tested at concentrations of 0 to 12.5 µm. These were incubated with GST-RBD supported on a Sepharose matrix and Ras in GTPγS or GDP. In the presence of the RNAs (lanes 3, 4 and 5 in FIG. 4; lane 3 is 20-pmol RNA, lane 4 200-pmol RNA and lane 5, 2000-pmol RNA) or in the absence of the RNAs (lanes 1 and 3 in FIG. 4; lane 1 was in the presence of GDP and lane 2 in the presence of GTP), the binding between GST-RBD and Ras was examined by immunoblotting with anti-Ras antibody RAS004.

In FIG. 4, "Ras" indicates Ras bound to GST-RBD, and "GST-RBD" indicates as a background that GST-RBD is solely present. As stated earlier, the RNA of SEQ ID NO:12 (D in FIG. 4) which is scarcely bound to GST-RBD did not inhibit the binding of Ras to GST-RBD even at the concentration of 12.5 μM. This was the same with the RNA of SEQ ID NO:11 (C in FIG. 4) in which the kd value was a micromol order.

On the other hand, the RNAs of SEQ ID NO:1 (A in FIG. 4) and SEQ ID NO:7 (B in FIG. 4) in group 1 effectively inhibited the interaction between Ras and RBD. The reason is considered to be that these RNAs were bound to RBD. And, the kd value of the GTP binding Ras and RBD of Raf-1 is 18 nM (Hermann, C., et al., J. Biol. Chem., 270, 2901–2905 (1995)), and the RNAs of SEQ ID NO:1 and SEQ ID NO:7 have the binding ability which is 10 times lower than that. Despite this, these RNAs inhibit the interaction between Ras and Raf-1.

Since these RNAs do not have an affinity for Ras or a Sepharose matrix, there is no possibility that these RNAs are bound to Ras or the Sepharose matrix to inhibit the binding between GST-RBD and Ras on the matrix. This fact proved the specific binding of these RNA aptamers to RBD.

Another in vitro selection was conducted by using a double-stranded DNA pool obtained by synthesizing a single-stranded DNA pool (200 pmols, $1.2 \times 10^{14}$ molecules) having a sequence of 5'-ggtaa tacga ctcac tatag ggagt ggagg aattc atcga ggcat-3' (SEQ ID NO:59) at the 5'-terminus and 5'-catat gcctt agcga cagca agctt ctgc-3' (SEQ ID NO:60) at the 3'-terminus and containing random 45 bases in the middle thereof and converting this single-stranded DNA pool to the double-stranded DNA pool by PCR.

Consequently, novel RNA atamers to be bound to Raf-1 RBD could be obtained. These sequences are as follows, and shown in SEQ ID NOs:25–28 of the Sequence Listing.

The Kd values of the RNAs shown in SEQ ID NOs:25, 26, and 28 among these RNAs and GST-RBD were as follows.

SEQ ID NO:25: 124 nM
SEQ ID NO:26: 295 nM
SEQ ID NO:28: 176 nM

And, the RNAs of SEQ ID NOs:25–28 all inhibited the binding between Ras and Raf-1 depending on the amounts.

SEQ ID NOs:25, 27, and 28 are different in the size of the 3'-terminus. From this fact, it is presumed that the RNAs of 99 to 81 bases (90 bases correspond to SEQ ID NO:27) up to SEQ ID NO:28 through the decrease by each one base from the 3'-side of SEQ ID NO:25 also have the activity.

Sequences of 45 bases corresponding to the random region were shown in SEQ ID NOs:53 and 54.

The RNA aptamers of SEQ ID NOs:25–28 obtained here can be provided through transcription from synthetic DNAs or through synthesis.

These RNA aptamers have the stronger binding activity and are made of the smaller number of RNA bases than the above-described RNA aptamers comprising approximately 60 bases. Accordingly, these are considered to be more profitable RNA aptamers.

An antibody bound to Raf-1 mutant free from a kinase activity or a kinase domain of Raf-1 has been used to study the role of Ras or Raf-1 in the cell signal transduction system (Kolch, W., et al., (1991) Nature 349, 426–428; Kolch, W., et al., (1996) Oncogene 13, 1305–1314).

The Raf-1 mutant capable of being bound to Ras without having the kinase activity not only inhibits the Ras-dependent Raf-1 activity but also blocks the wide-ranging signal transduction systems including Ras. This is because the mutant inhibits the binding of Raf-1 and also has an influence on various downstream effectors of GTP-binding Ras.

Likewise, a monoclonal antibody bound to an epitope of a kinase domain of Raf-1 inhibits all signal transduction systems including Raf-1. This is because Raf-1 is activated

```
SEQ ID NO:25 gggaguggag gaauucaucg aggcauaugu cgacuccguc uuccuucaaa ccaguuauaa    60
auugguuuua gcauaugccu uagcgacagc aagcuucugc                        100

SEQ ID NO:26 gggaguggag gaauucaucg aggcaugacc ucccguggca guagggguaa aaauuaucuu  60
ccuacacuuc ucaugccuua gcgacagcaa gcuucugc                          98

SEQ ID NO:27 gggaguggag gaauucaucg aggcauaugu cgacuccguc uuccuucaaa ccaguuauaa  60
auugguuuua gcauaugccu uagcgacagc                                   90

SEQ ID NO:28 gggaguggag gaauucaucg aggcauaugu cgacuccguc uuccuucaaa ccaguuauaa  60
auugguuuua gcauaugccu                                              80
``` not only with GTP binding Ras but also through a route having no bearing on Ras (Kolch, W., et al., (1996) Oncogene 13, 1305–1314).

From this standpoint as well, it is said that the RNA aptamer to RBD in the present invention can specifically inhibit the binding between the Ras and Raf-1 without having any effect on the kinase activity of Ras or Raf-1 by the other signaling pathways.

Further, the RNA aptamers of the present invention can be expressed within cells (Good, P. D., et al., (1997) Gene Ther. 4,45–54), and can be applied to a wide-ranging field.

Thus, the RNA aptamers of the present invention specifically block RBD of "target proteins of Ras", more preferably Raf-1. Not only it can be used in an agent for controlling intracellular signal transduction or a method of controlling cell signaling pathway, but also it is especially suited for the field of treatment, prevention or diagnosis of various diseases in which the signal transduction system participates.

When the nucleic acid molecular seed of the present invention is used in controlling the cell signal transduction system, the nucleic acid of the present invention may directly be introduced into desired cells. It can also be introduced into cells by being inserted into viruses or the like.

Further, it is also possible that the RNA is introduced not directly but in the form of a DNA. When the nucleic acid molecular seed of the present invention is used as a pharmaceutical composition, it can parenterally be administered as such, or it can be administered by being inserted into viruses or various vectors in the form of a DNA. In these administration forms, the pharmaceutical composition can also be provided using a pharmaceutically acceptable carrier.

The pharmaceutical composition of the present invention is useful for treatment, prevention or diagnosis of various diseases in which the cell signal transduction system participates, especially malignant tumors and inflammatory diseases.

EXAMPLES

The present invention is illustrated more specifically with reference to the following Examples. However, the present invention is not limited to these Examples.

Example 1

Purification of a Protein

Glutathione S-transferase (GST) and a fusion protein of RBD (51 to 131 amino acid moiety of Raf-1) and GST (hereinafter referred to as GST-RBD) were expressed in *E. coli* strains BL21 and BL21DE3 respectively, and purified by chromatography using a column of glutathione-Sepharose 4B (made by Amerhsam Pharmacia Biotec) and HQ proth (perceptive) (Shirouzu M., et al., J. Biol. Chem., 273, 7737–7742 (1998)).

As wild type Ha-Ras protein, a protein obtained from *E. coli* strain BL21 was purified by column chromatography using DAEA-Sephacell, Sephadex G75 and Resource QFPLC (made by Amersham Pharmacia Biotec) (Shirouzu M., et al., J. Biol. Chem., 273, 7737–7742 (1998); Shirouzu M., et al., Oncogene, 7, 475–480 (1992); Ito, Y., et al., Biochemistry, 36, 9109–9119 (1997)).

The purity of these proteins was identified through SDS-PAGE by staining with Coomassie Blue and/or silver. The purified protein was stored in 50% glycerol at −30° C.

Example 2

In vitro Selection

A pool of DNAs containing random 60 bases were prepared. These DNAs have sequences 5'-GCCGGAAT-TCTAATACGACTCACTATAGGGAGATCA-GAATAAACGCTCAA-3' (SEQ ID NO:57) and 5'-TTCGA-CATGAGGCCCCTGCAGGGCG-3' (SEQ ID NO:62) at both termini for in vitro transcription and amplification by PCR.

These RNAs were heated at 75° C. for 3 minutes, then ice-cooled, and incubated in a binding buffer (5 mM $MgCl_2$-containing phosphate buffer physiological saline solution) containing GST-RBD and glutathione-Sepharose 4B beads. The RNAs having GST-RBD bound thereto were recovered with glutathione-Sepharose beads. The beads were cleaned with a cleaning buffer (20 mM Tris-HCl pH 7.5, 5 mM $MgCl_2$ and 150 mM NaCl), and the RNAs on the beads were eluted with boiling water.

The 1st through 13th rounds were conducted in this manner, provided that in order to remove the RNAs bound to GST and/or the beads alone, the RNAs were passed through glutathione-Sepharose beads having supported thereon GST only before the incubation of GST-RBD (3rd to 13th rounds) and after the elution (7th to 13th rounds).

The eluate was subjected to reverse transcription, and amplified through PCR. The RNA pool for the next round was prepared through in vitro transcription from the cDNA amplified. The 13th round and those following for selection were conducted by a filter binding method. The RNA pool (heated at 75° C. for 3 minutes, and cooled to room temperature) and GST-RBD were incubated in a binding buffer at 37° C. for 1 hour. The RNAs bound to GST-RBD were separated by being bound to a nitrocellulose filter. The RNAs were eluted with a buffer containing 7 M urea (Hirao, I., et al., Mol. Diversity, (under printing)). In order to remove the RNAs bound to the filter, the RNAs were passed through the filter before the amplification.

Example 3

Nitrocellulose Filter Binding Assay

RNAs were obtained through the in vitro transcription with a T7 RNA polymerase using $[\alpha-^{32}P]UTP$. The RNA (0.8 µM) and its protein were incubated in 50 µl of a binding buffer at 37° C. for 1 hour. A part (50 µl) of the solution was moved on a filter, and cleaned three times with 200 µl of a cleaning buffer.

In order to determine a dissociation constant, 1.6 nM of the RNA of which the 5'-terminus was labeled with $[\gamma-^{32}P]$ ATP and GST-RBD at various concentrations were incubated. The radiation dose on the filter was measured using a Fuji BAS2500 bio-imaging analyzer.

Example 4

Inhibitory Activity

One microgram of GST-RBD in 160 µl of a binding buffer containing 0.05% Triton X-100 was mixed with 10 µl of a glutathione-Sepharse bead suspension in a phosphate buffer physiological saline solution. The mixture was incubated at 4° C. for 30 minutes. After the gentle centrifugation, the supernatant liquid was discarded. A binding buffer solution containing 40 ng of Ras (this is bound through GTPγS or GDP as described in a literature (Koide, H., et al., Proc. Natl. Acad. Sci. USA, 90, 8683–8686 (1993) and 160 µl of the RNA was added to the remaining beads, and incubated at 4° C. for 30 minutes. After the incubation, the beads were cleaned with 500 µl of a cleaning buffer. The bound protein was eluted form the beads through separation using a Laemmli's buffer, and subjected to 15% SDS-PAGE. The product was subjected to immunoblotting with anti-Ras antibody RAS004 (Moodie, S. A., et al., Science, 260, 1658–1661 (1993)), and visualized with an ECL immune detector (manufactured by Amersham Pharmacia Biotec).

Example 5

Formation of an RNA Pool

A single-stranded DNA (200 pmols, $1.2 \times 10^{14}$ molecules) containing random 45 bases and having a sequence 5'-ggtaa tacga ctcac tatag ggagt ggagg aattc atcga ggcat-3' (SEQ ID NO:59) at the 5' terminus and a sequence 5'-catat gcctt agcga cagca agctt ctgc-3' (SEQ ID NO:60) at the 3'-terminus was subjected to PCR using 2 primers, 5'-ggtaa tacga ctcac tatag ggagt ggagg aattc atcg-3' (SEQ ID NO:63) and 5'-gcaga agctt gctgt cgcta aggc-3' (SEQ ID NO:64), and then transcribed with a T7 RNA polymerase to form a first RNA pool.

Example 6

Selection of RNA Bound to Raf-1RBD

Three micromols (1,800 pmols) of the RNA pool heated at 7520 C. for 3 minutes and then ice-cooled and 1 µM (600 pmols) of GST-RBD were incubated in 600 µl of a binding buffer at 37° C. for 1 hour. The culture was filtered with a nitrocellulose filter, and the filter was cleaned three times with 300 µl of a cleaning buffer. Thereafter, the RNAs on the filter were eluted with a buffer containing 7 M urea. After the reverse transcription, PCR was conducted at 12 cycles.

The reagents used here are as follows.

GST-RBD: A fusion protein of RBD (51 to 131 amino acid moiety of Raf-1) and glutathione-S-transferase is described in a literature (Shirouzu, M., et al., (1998) J. Biol. Chem. 273, 7737–7742).

binding buffer: 5 mM $MgCl_2$-containing phosphate buffer physiological saline solution cleaning buffer: 2 0mM Tris-HCl pH 7.5, 5 mM $MgCl_2$ and 150 mM NaCl

Example 7

RNAS of Sequence Nos. 25 and 26

Selection of RNAs bound to Raf-1 RBD from the first RNA pool in Example 6, reverse transcription of RNAs to DNAs, amplification and transcription of DNAs to RNAs were repeated 10 times to obtain RNAs of sequence Nos. 25 and 26 of the Sequence Listing.

Example 8

RNAs of SEQ ID NOs:27 and 28

DNAs which had a complementary sequence of an RNA of SEQ ID NO:25 and of which the 3-terminus side was shortened were obtained by PCR using a primer 5'-ggtaa tacga ctcac tatag ggagt ggagg aattc atcg-3' (SEQ ID NO:63) and a primer 5'-gctgt cgcta agga tatgc taaaa c-3' (SEQ ID NO:65) or 5'-aggca tatgc taaaa ccaat ttata ac-3' (SEQ ID NO:66). From these DNAs, RNAs of SEQ ID NOs:27 and 28 of the Sequence Listing were obtained.

Example 9

Cloning and Determination of a Sequence

A DNA was cloned using a TOPO TA cloning kit, and the sequence was determined with an automated DNA sequencer.

Example 10

Measurement of a Kd Value

An RNA (4 nM) of which the 5'-terminus was labeled and 50 to 1,250 nM of GST-RBD were incubated in 600 µl of a binding buffer at 37° C. for 30 minutes. The culture was filtered with a nitrocellulose filter, and the radioactivity on the filter was measured. The Kd value was calculated using a software: Kalleider Graph (Bell, S. D., et al., (1998) J. Biol. Chem. 273, 14309–14314).

Example 11

Binding Inhibition Experiment

GST-RBD (20 pmols) in 160 µl of a binding buffer containing 0.05% Triton X-100 and 10 µl of a phosphate buffer physiological saline solution containing glutathione-Sepharose 4B beads were mixed, and the mixture was incubated at 4° C. for 30 minutes. The beads were separated, and incubated with 20 pmols of Ras and an RNA (0, 20, 100 and 200 pmols) in 160 µl of a binding buffer (5 mM $MgCl_2$-containing phosphate buffer physiological saline solution) at 4° C. for 30 minutes. After the beads were cleaned, the bound protein was eluted with a Laemmli's buffer, subjected to SDS-PAGE, then immunoblotted using anti-Ras antibody RAS004 (Kanai, T., et al., (1987) Jpn. J. Cancer Res. 78, 1314–1318), and visualized with an EXL immune director.

In the RNAs of SEQ ID NOs:25–28, the decrease in the amount of Ras was observed according to the RNA amount.

INDUSTRIAL APPLICABILITY

The present invention provides RNAs which are specifically bound to target proteins of Ras such as Raf-1 and the like and which further inhibit the binding to Ras, and a method of specifically inhibiting an intracellular signaling pathway using these RNAs. The present invention can not only clarify the signaling pathway through the specific route of cells but also provide a pharmaceutical composition having less side effects.

What is claimed is:

1. An isolated RNA which specifically binds to Raf-1 protein, wherein the RNA comprises at least one sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:25, SEQ ID NO:26, SEQ ID NO:27, SEQ ID NO:28, and a sequence of 81–99 nucleotides which is obtained through the decrease of one base each from the 3' end of SEQ NO:25.

2. The isolated RNA of claim 1, wherein the RNA specifically binds to a Ras-binding domain of Raf-1.

3. The isolated RNA of claim 1, wherein the RNA comprises at least one sequence selected from the group consisting of SEQ ID NO:1, SEQ ID NO:2, SEQ ID NO:3, SEQ ID NO:4, SEQ ID NO:5, SEQ ID NO:6, SEQ ID NO:25, SEQ ID NO:26, and a sequence of 81–99 nucleotides which is obtained through the decrease of one base each from the 3' end of SEQ ID NO:25.

4. An isolated nucleic acid comprising a sequence which is fully complementary to the isolated RNA of claim 1.

5. An isolated nucleic acid comprising a sequence which is fully complementary to the isolated RNA of claim 3.

* * * * *

SEQUENCE LISTING

<160> NUMBER OF SEQ ID NOS: 66

<210> SEQ ID NO 1
<211> LENGTH: 108
<212> TYPE: RNA
<213> ORGANISM: Artificial
<220> FEATURE:
<223> OTHER INFORMATION: RNA aptamer

<400> SEQUENCE: 1
gggagaucag aauaaacgcu caacugauca auggcguaca auggauucgu ucucauaacc    60 aaaaccuua ccccuuggac ugauucgaca ugaggccccu gcagggcg                 108

<210> SEQ ID NO 2
<211> LENGTH: 107
<212> TYPE: RNA
<213> ORGANISM: Artificial
<220> FEATURE:
<223> OTHER INFORMATION: RNA aptamer

<400> SEQUENCE: 2
gggagaucag aauaaacgcu caacugauca auggcguaca auggauucgu ucucauaacc    60 aaaaccuua ccccuggacu gauucgacau gaggccccug cagggcg                  107

<210> SEQ ID NO 3
<211> LENGTH: 108
<212> TYPE: RNA
<213> ORGANISM: Artificial
<220> FEATURE:
<223> OTHER INFORMATION: RNA aptamer

<400> SEQUENCE: 3
gggagaucag aauaaacgcu caacugauca auggcguaca auggauucgu ucucauaacc    60 aaaaccuua ccccuuggac ugcuucgaca ugaggccccu gcagggcg                 108

<210> SEQ ID NO 4
<211> LENGTH: 108
<212> TYPE: RNA
<213> ORGANISM: Artificial
<220> FEATURE:
<223> OTHER INFORMATION: RNA aptamer

<400> SEQUENCE: 4
gggagaucag aauaaacgcu caacugauca auggcguaca auggauucgc ucucauaacc    60 aaaaccuua ccccuuggac ugcuucgaca ugaggccccu gcagggcg                 108

<210> SEQ ID NO 5
<211> LENGTH: 108
<212> TYPE: RNA
<213> ORGANISM: Artificial
<220> FEATURE:
<223> OTHER INFORMATION: RNA aptamer

<400> SEQUENCE: 5
gggagaucag aauaaacgcu caacugauca auggcguaca auggauucgu ucucauaacc    60 aaaaccuua cuccuuggac ugcuucgaca ugaggccccu gcagggcg                 108

<210> SEQ ID NO 6
<211> LENGTH: 108
<212> TYPE: RNA
<213> ORGANISM: Artificial

```
<220> FEATURE:
<223> OTHER INFORMATION: RNA aptamer

<400> SEQUENCE: 6
gggagaucag aauaaacgcu caacugauca auggcguaca auggauucgu ucucauaacc      60 aaaaccuua ccccuuggac uguuucgaca ugaggcsccu gcagggcg                   108

<210> SEQ ID NO 7
<211> LENGTH: 108
<212> TYPE: RNA
<213> ORGANISM: Artificial
<220> FEATURE:
<223> OTHER INFORMATION: RNA aptamer

<400> SEQUENCE: 7
gggagaucag aauaaacgcu caauugacuc aauggcguac aauggauucg uucucauaac      60
caaaacccuu accccuugga cguucgaca ugaggccccu gcagggcg                    108

<210> SEQ ID NO 8
<211> LENGTH: 108
<212> TYPE: RNA
<213> ORGANISM: Artificial
<220> FEATURE:
<223> OTHER INFORMATION: RNA aptamer

<400> SEQUENCE: 8
gggagaucag aauaaacgcu caauugaaga ucguacaaug gauucgauca uaacccgaag      60
uuuuuaaaca cucuuuaccu guauucgaca ugaggccccu gcagggcg                   108

<210> SEQ ID NO 9
<211> LENGTH: 108
<212> TYPE: RNA
<213> ORGANISM: Artificial
<220> FEATURE:
<223> OTHER INFORMATION: RNA aptamer

<400> SEQUENCE: 9
gggagaucag aauaaacgcu caaucgaguc cacgaacauu acauauuuga acacuucagc      60
accgaacaug cuuaguacua uccuucgaca ugaggccccu gcagggcg                   108

<210> SEQ ID NO 10
<211> LENGTH: 108
<212> TYPE: RNA
<213> ORGANISM: Artificial
<220> FEATURE:
<223> OTHER INFORMATION: RNA aptamer

<400> SEQUENCE: 10
gggagaucag aauaaacgcu caauauuacc auagccuuga gguaaacaau uuagcacacc      60
ugaauacacg aacuaugaac ucauucgaca ugaggccccu gcagggcg                   108

<210> SEQ ID NO 11
<211> LENGTH: 107
<212> TYPE: RNA
<213> ORGANISM: Artificial
<220> FEATURE:
<223> OTHER INFORMATION: RNA aptamer

<400> SEQUENCE: 11
gggagaucag aauaaacgcu caacuugagc caauuaaaag auuuacaaca agaacaugaa      60
cgugacagcg auaauaauac gauucgacau gaggccccug cagggcg                    107
```

<210> SEQ ID NO 12
<211> LENGTH: 108
<212> TYPE: RNA
<213> ORGANISM: Artificial
<220> FEATURE:
<223> OTHER INFORMATION: RNA aptamer

<400> SEQUENCE: 12
gggagaucag aauaaacgcu caagcgacaa gcagcagaua aaguugagcg caacgccgcu    60
acagaaccaa auuaacaugu auguucgaca ugaggcsccu gcagggcg                108

<210> SEQ ID NO 13
<211> LENGTH: 107
<212> TYPE: RNA
<213> ORGANISM: Artificial
<220> FEATURE:
<223> OTHER INFORMATION: RNA aptamer

<400> SEQUENCE: 13
gggagaucag aauaaacgcu caaucgaaag uaaguccgau acaacacaua accuauuauu    60
uagcagcgau aauacaaaua aguucgacau gaggcsccug cagggcg                 107

<210> SEQ ID NO 14
<211> LENGTH: 108
<212> TYPE: RNA
<213> ORGANISM: Artificial
<220> FEATURE:
<223> OTHER INFORMATION: RNA aptamer

<400> SEQUENCE: 14
gggagaucag aauaaacgcu caagcaguaa uccacuugua auugaaugua gaugccauau    60
agaguuauua guaauccgaa uuguucgaca ugaggcsccu gcagggcg                108

<210> SEQ ID NO 15
<211> LENGTH: 108
<212> TYPE: RNA
<213> ORGANISM: Artificial
<220> FEATURE:
<223> OTHER INFORMATION: RNA aptamer

<400> SEQUENCE: 15
gggagaucag aauaaacgcu caacguagua gcacaccaug accuauuaaa ucugcuucgc    60
aauguaccuu aacacauaau caguucgaca ugaggcsccu gcagggcg                108

<210> SEQ ID NO 16
<211> LENGTH: 108
<212> TYPE: RNA
<213> ORGANISM: Artificial
<220> FEATURE:
<223> OTHER INFORMATION: RNA aptamer

<400> SEQUENCE: 16
gggagaucag aauaaacgcu caagaaugac uaauaauuac aacagauaac cuuacucuug    60
auaaaugcuu ugcuuuuggu uaauucgaca ugaggcsccu gcagggcg                108

<210> SEQ ID NO 17
<211> LENGTH: 108
<212> TYPE: RNA
<213> ORGANISM: Artificial
<220> FEATURE:
<223> OTHER INFORMATION: RNA aptamer

<400> SEQUENCE: 17

```
gggagaucag aauaaacgcu caaucuucga aguccaugac ugcaaaacca gauaguccua    60
aucucaauua ucagucccaa guauucgaca ugaggcsccu gcagggcg               108
```

<210> SEQ ID NO 18
<211> LENGTH: 108
<212> TYPE: RNA
<213> ORGANISM: Artificial
<220> FEATURE:
<223> OTHER INFORMATION: RNA aptamer

<400> SEQUENCE: 18

```
gggagaucag aauaaacgcu caaacacucu aaauuguggu acuaagggag uaagggcaac    60
uacgaagacg ugcaaggaua aaguucgaca ugaggccccu gcagggcg               108
```

<210> SEQ ID NO 19
<211> LENGTH: 107
<212> TYPE: RNA
<213> ORGANISM: Artificial
<220> FEATURE:
<223> OTHER INFORMATION: RNA aptamer

<400> SEQUENCE: 19

```
gggagaucag aauaaacgcu caauuugccu cgacggucug cgaauagaac gcgaaccgug    60
auuaguguac aaggauucgg uuucgacau gaggccccug cagggcg                107
```

<210> SEQ ID NO 20
<211> LENGTH: 106
<212> TYPE: RNA
<213> ORGANISM: Artificial
<220> FEATURE:
<223> OTHER INFORMATION: RNA aptamer

<400> SEQUENCE: 20

```
gggagaucag aauaaacgcu caagucgcag cagaaauauc aucgcaaaac cucaauugca    60
ucucauguau aucuagucca auucgacaug aggccccugc agggcg                106
```

<210> SEQ ID NO 21
<211> LENGTH: 105
<212> TYPE: RNA
<213> ORGANISM: Artificial
<220> FEATURE:
<223> OTHER INFORMATION: RNA aptamer

<400> SEQUENCE: 21

```
gggagaucag aauaaacgcu caacgaacau cuggaguaau caucuuaaua accucauuaa    60
ccuuuacacu uucuaaacua uucgacauga ggccccugca gggcg                  105
```

<210> SEQ ID NO 22
<211> LENGTH: 108
<212> TYPE: RNA
<213> ORGANISM: Artificial
<220> FEATURE:
<223> OTHER INFORMATION: RNA aptamer

<400> SEQUENCE: 22

```
gggagaucag aauaaacgcu caaggguaag ggugagcagu ucaagauggu aacuggcauu    60
cauuugaaga aagguuggua gacuucgaca ugaggccccu gcagggcg               108
```

<210> SEQ ID NO 23
<211> LENGTH: 108
<212> TYPE: RNA

<213> ORGANISM: Artificial
<220> FEATURE:
<223> OTHER INFORMATION: RNA aptamer

<400> SEQUENCE: 23
gggagaucag aauaaacgcu caaggguaag ggugagcagu ucaagauggu aaccggcauu    60
cauuugaaga aagguuggua aacuucgaca ugaggcsccu gcagggcg    108

<210> SEQ ID NO 24
<211> LENGTH: 101
<212> TYPE: RNA
<213> ORGANISM: Artificial
<220> FEATURE:
<223> OTHER INFORMATION: RNA aptamer

<400> SEQUENCE: 24
gggagaucag aauaaacgcu caacuuggug uaguguucaa gugagauaua guauaagguu    60
auuguugugc gaacgguucg acaugaggcc ccugcagggc g    101

<210> SEQ ID NO 25
<211> LENGTH: 100
<212> TYPE: RNA
<213> ORGANISM: Artificial
<220> FEATURE:
<223> OTHER INFORMATION: RNA aptamer

<400> SEQUENCE: 25
gggaguggag gaauucaucg aggcauaugu cgacuccguc uuccuucaaa ccaguuauaa    60
auugguuuua gcauaugccu uagcgacagc aagcuucugc    100

<210> SEQ ID NO 26
<211> LENGTH: 98
<212> TYPE: RNA
<213> ORGANISM: Artificial
<220> FEATURE:
<223> OTHER INFORMATION: RNA aptamer

<400> SEQUENCE: 26
gggaguggag gaauucaucg aggcaugacc ucccguggca guagggguaa aaauuaucuu    60
ccuacacuuc ucaugccuua gcgacagcaa gcuucugc    98

<210> SEQ ID NO 27
<211> LENGTH: 90
<212> TYPE: RNA
<213> ORGANISM: Artificial
<220> FEATURE:
<223> OTHER INFORMATION: RNA aptamer

<400> SEQUENCE: 27
gggaguggag gaauucaucg aggcauaugu cgacuccguc uuccuucaaa ccaguuauaa    60
auugguuuua gcauaugccu uagcgacagc    90

<210> SEQ ID NO 28
<211> LENGTH: 80
<212> TYPE: RNA
<213> ORGANISM: Artificial
<220> FEATURE:
<223> OTHER INFORMATION: RNA aptamer

<400> SEQUENCE: 28
gggaguggag gaauucaucg aggcauaugu cgacuccguc uuccuucaaa ccaguuauaa    60
auugguuuua gcauaugccu    80

```
<210> SEQ ID NO 29
<211> LENGTH: 60
<212> TYPE: RNA
<213> ORGANISM: Artificial
<220> FEATURE:
<223> OTHER INFORMATION: RNA aptamer

<400> SEQUENCE: 29
cugaucaaug gcguacaaug gauucguucu cauaaccaaa acccuuaccc cuuggacuga      60

<210> SEQ ID NO 30
<211> LENGTH: 59
<212> TYPE: RNA
<213> ORGANISM: Artificial
<220> FEATURE:
<223> OTHER INFORMATION: RNA aptamer

<400> SEQUENCE: 30
cugaucaaug gcguacaaug gauucguucu cauaaccaaa acccuuaccc cuggacuga       59

<210> SEQ ID NO 31
<211> LENGTH: 60
<212> TYPE: RNA
<213> ORGANISM: Artificial
<220> FEATURE:
<223> OTHER INFORMATION: RNA aptamer

<400> SEQUENCE: 31
cugaucaaug gcguacaaug gauucguucu cauaaccaaa acccuuaccc cuuggacugc      60

<210> SEQ ID NO 32
<211> LENGTH: 60
<212> TYPE: RNA
<213> ORGANISM: Artificial
<220> FEATURE:
<223> OTHER INFORMATION: RNA aptamer

<400> SEQUENCE: 32
cugaucaaug gcguacaaug gauucgcucu cauaaccaaa acccuuaccc cuuggacugc      60

<210> SEQ ID NO 33
<211> LENGTH: 60
<212> TYPE: RNA
<213> ORGANISM: Artificial
<220> FEATURE:
<223> OTHER INFORMATION: RNA aptamer

<400> SEQUENCE: 33
cugaucaaug gcguacaaug gauucguucu cauaaccaaa acccuuacuc cuuggacugc      60

<210> SEQ ID NO 34
<211> LENGTH: 60
<212> TYPE: RNA
<213> ORGANISM: Artificial
<220> FEATURE:
<223> OTHER INFORMATION: RNA aptamer

<400> SEQUENCE: 34
cugaucaaug gcguacaaug gauucguucu cauaaccaaa acccuuaccc cuuggacugu      60

<210> SEQ ID NO 35
<211> LENGTH: 60
<212> TYPE: RNA
<213> ORGANISM: Artificial
<220> FEATURE:
```

<223> OTHER INFORMATION: RNA aptamer

<400> SEQUENCE: 35
uugacucaau ggcguacaau ggauucguuc ucauaaccaa aacccuuacc ccuuggacug       60

<210> SEQ ID NO 36
<211> LENGTH: 60
<212> TYPE: RNA
<213> ORGANISM: Artificial
<220> FEATURE:
<223> OTHER INFORMATION: RNA aptamer

<400> SEQUENCE: 36
uugaagaucg uacaauggau ucgaucauaa cccgaaguuu uuaaacacuc uuuaccugua       60

<210> SEQ ID NO 37
<211> LENGTH: 60
<212> TYPE: RNA
<213> ORGANISM: Artificial
<220> FEATURE:
<223> OTHER INFORMATION: RNA aptamer

<400> SEQUENCE: 37
ucgaguccac gaacauuaca uauuugaaca cuucagcacc gaacaugcuu aguacuaucc       60

<210> SEQ ID NO 38
<211> LENGTH: 60
<212> TYPE: RNA
<213> ORGANISM: Artificial
<220> FEATURE:
<223> OTHER INFORMATION: RNA aptamer

<400> SEQUENCE: 38
uauuaccaua gccuugaggu aaacaauuua gcacaccuga auacacgaac uaugaacuca       60

<210> SEQ ID NO 39
<211> LENGTH: 59
<212> TYPE: RNA
<213> ORGANISM: Artificial
<220> FEATURE:
<223> OTHER INFORMATION: RNA aptamer

<400> SEQUENCE: 39
cuugagccaa uuaaaagauu uacaacaaga acaugaacgu gacagcgaua auaauacga       59

<210> SEQ ID NO 40
<211> LENGTH: 60
<212> TYPE: RNA
<213> ORGANISM: Artificial
<220> FEATURE:
<223> OTHER INFORMATION: RNA aptamer

<400> SEQUENCE: 40
gcgacaagca gcagauaaag uugagcgcaa cgccgcuaca gaaccaaauu aacauguaug       60

<210> SEQ ID NO 41
<211> LENGTH: 59
<212> TYPE: RNA
<213> ORGANISM: Artificial
<220> FEATURE:
<223> OTHER INFORMATION: RNA aptamer

<400> SEQUENCE: 41
ucgaaaguaa guccgauaca acacauaacc uauuauuuag cagcgauaau acaaauaag       59

<210> SEQ ID NO 42
<211> LENGTH: 60
<212> TYPE: RNA
<213> ORGANISM: Artificial
<220> FEATURE:
<223> OTHER INFORMATION: RNA aptamer

<400> SEQUENCE: 42
gcaguaaucc acuuguaauu gaauguagau gccauauaga guuauuagua auccgaauug        60

<210> SEQ ID NO 43
<211> LENGTH: 60
<212> TYPE: RNA
<213> ORGANISM: Artificial
<220> FEATURE:
<223> OTHER INFORMATION: RNA aptamer

<400> SEQUENCE: 43
cguaguagca caccaugacc uauuaaaucu gcuucgcaau guaccuuaac acauaaucag        60

<210> SEQ ID NO 44
<211> LENGTH: 60
<212> TYPE: RNA
<213> ORGANISM: Artificial
<220> FEATURE:
<223> OTHER INFORMATION: RNA aptamer

<400> SEQUENCE: 44
gaaugacuaa uaauuacaac agauaaccuu acucuugaua aaugcuuugc uuuugguuaa        60

<210> SEQ ID NO 45
<211> LENGTH: 60
<212> TYPE: RNA
<213> ORGANISM: Artificial
<220> FEATURE:
<223> OTHER INFORMATION: RNA aptamer

<400> SEQUENCE: 45
ucuucgaagu ccaugacugc aaaaccagau aguccuaauc ucaauuauca gucccaagua        60

<210> SEQ ID NO 46
<211> LENGTH: 60
<212> TYPE: RNA
<213> ORGANISM: Artificial
<220> FEATURE:
<223> OTHER INFORMATION: RNA aptamer

<400> SEQUENCE: 46
acacucuaaa uugugguacu aagggaguaa gggcaacuac gaagacgugc aaggauaaag        60

<210> SEQ ID NO 47
<211> LENGTH: 59
<212> TYPE: RNA
<213> ORGANISM: Artificial
<220> FEATURE:
<223> OTHER INFORMATION: RNA aptamer

<400> SEQUENCE: 47
uuugccucga cggucugcga auagaacgcg aaccugauu aguguacaag gauucgguu         59

<210> SEQ ID NO 48
<211> LENGTH: 58
<212> TYPE: RNA
<213> ORGANISM: Artificial
<220> FEATURE:
<223> OTHER INFORMATION: RNA aptamer

```
<400> SEQUENCE: 48
gucgcagcag aaauaucauc gcaaaaccuc aauugcaucu cauguauauc uaguccaa        58

<210> SEQ ID NO 49
<211> LENGTH: 57
<212> TYPE: RNA
<213> ORGANISM: Artificial
<220> FEATURE:
<223> OTHER INFORMATION: RNA aptamer

<400> SEQUENCE: 49
cgaacaucug gaguaaucau cuuaauaacc ucauuaaccu uuacacuuuc uaaacua        57

<210> SEQ ID NO 50
<211> LENGTH: 60
<212> TYPE: RNA
<213> ORGANISM: Artificial
<220> FEATURE:
<223> OTHER INFORMATION: RNA apatmer

<400> SEQUENCE: 50
ggguaagggu gagcaguuca agaugguaac uggcauucau uugaagaaag guugguagac        60

<210> SEQ ID NO 51
<211> LENGTH: 60
<212> TYPE: RNA
<213> ORGANISM: Artificial
<220> FEATURE:
<223> OTHER INFORMATION: RNA aptamer

<400> SEQUENCE: 51
ggguaagggu gagcaguuca agaugguaac cggcauucau uugaagaaag guugguaaac        60

<210> SEQ ID NO 52
<211> LENGTH: 53
<212> TYPE: RNA
<213> ORGANISM: Artificial
<220> FEATURE:
<223> OTHER INFORMATION: RNA aptamer

<400> SEQUENCE: 52
cuugguguag uguucaagug agauauagua uaagguuauu guugugcgaa cgg        53

<210> SEQ ID NO 53
<211> LENGTH: 45
<212> TYPE: RNA
<213> ORGANISM: Artificial
<220> FEATURE:
<223> OTHER INFORMATION: RNA aptamer

<400> SEQUENCE: 53
augucgacuc cgucuuccuu caaaccaguu auaaauuggu uuuag        45

<210> SEQ ID NO 54
<211> LENGTH: 45
<212> TYPE: RNA
<213> ORGANISM: Artificial
<220> FEATURE:
<223> OTHER INFORMATION: RNA aptamer

<400> SEQUENCE: 54
gaccucccgu ggcaguaggg guaaaaauua ucuuccuaca cuucu        45

<210> SEQ ID NO 55
<211> LENGTH: 23
```

```
<212> TYPE: RNA
<213> ORGANISM: Artificial
<220> FEATURE:
<223> OTHER INFORMATION: primer for cDNA

<400> SEQUENCE: 55
gggagaucag aauaaacgcu caa                                             23

<210> SEQ ID NO 56
<211> LENGTH: 25
<212> TYPE: RNA
<213> ORGANISM: Artificial
<220> FEATURE:
<223> OTHER INFORMATION: primer for cDNA

<400> SEQUENCE: 56
uucgacauga ggccccugca gggcg                                           25

<210> SEQ ID NO 57
<211> LENGTH: 50
<212> TYPE: DNA
<213> ORGANISM: Artificial
<220> FEATURE:
<223> OTHER INFORMATION: PCR primer

<400> SEQUENCE: 57
gccggaattc taatacgact cactataggg agatcagaat aaacgctcaa                50

<210> SEQ ID NO 58
<211> LENGTH: 25
<212> TYPE: DNA
<213> ORGANISM: Artificial
<220> FEATURE:
<223> OTHER INFORMATION: PCR primer

<400> SEQUENCE: 58
cgccctgcag gggcctcatg tcgaa                                           25

<210> SEQ ID NO 59
<211> LENGTH: 45
<212> TYPE: DNA
<213> ORGANISM: Artificial
<220> FEATURE:
<223> OTHER INFORMATION: PCR primer

<400> SEQUENCE: 59
ggtaatacga ctcactatag ggagtggagg aattcatcga ggcat                     45

<210> SEQ ID NO 60
<211> LENGTH: 29
<212> TYPE: DNA
<213> ORGANISM: Artificial
<220> FEATURE:
<223> OTHER INFORMATION: PCR primer

<400> SEQUENCE: 60
catatgcctt agcgacagca agcttctgc                                       29

<210> SEQ ID NO 61
<211> LENGTH: 108
<212> TYPE: RNA
<213> ORGANISM: Artificial
<220> FEATURE:
<223> OTHER INFORMATION: random RNA pool
<220> FEATURE:
<221> NAME/KEY: misc_feature
<222> LOCATION: (24)..(83)
```

```
<223> OTHER INFORMATION: n is a, c, g, or t

<400> SEQUENCE: 61
gggagaucag aauaaacgcu caannnnnnn nnnnnnnnnn nnnnnnnnnn nnnnnnnnnn      60
nnnnnnnnnn nnnnnnnnnn nnnuucgaca ugaggcccu gcagggcg                  108

<210> SEQ ID NO 62
<211> LENGTH: 25
<212> TYPE: DNA
<213> ORGANISM: Artificial
<220> FEATURE:
<223> OTHER INFORMATION: primer

<400> SEQUENCE: 62
ttcgacatga ggcccctgca gggcg                                           25

<210> SEQ ID NO 63
<211> LENGTH: 39
<212> TYPE: DNA
<213> ORGANISM: Artificial
<220> FEATURE:
<223> OTHER INFORMATION: primer

<400> SEQUENCE: 63
ggtaatacga ctcactatag ggagtggagg aattcatcg                            39

<210> SEQ ID NO 64
<211> LENGTH: 24
<212> TYPE: DNA
<213> ORGANISM: Artificial
<220> FEATURE:
<223> OTHER INFORMATION: primer

<400> SEQUENCE: 64
gcagaagctt gctgtcgcta aggc                                            24

<210> SEQ ID NO 65
<211> LENGTH: 26
<212> TYPE: DNA
<213> ORGANISM: Artificial
<220> FEATURE:
<223> OTHER INFORMATION: primer

<400> SEQUENCE: 65
gctgtcgcta aggcatatgc taaaac                                          26

<210> SEQ ID NO 66
<211> LENGTH: 27
<212> TYPE: DNA
<213> ORGANISM: Artificial
<220> FEATURE:
<223> OTHER INFORMATION: primer

<400> SEQUENCE: 66
aggcatatgc taaaaccaat ttataac                                         27
```